United States Patent
Chalupper et al.

(10) Patent No.: US 6,920,227 B2
(45) Date of Patent: Jul. 19, 2005

(54) ACTIVE NOISE SUPPRESSION FOR A HEARING AID DEVICE WHICH CAN BE WORN IN THE EAR OR A HEARING AID DEVICE WITH OTOPLASTIC WHICH CAN BE WORN IN THE EAR

(75) Inventors: Josef Chalupper, Paunzhausen (DE); Werner Lipski, Stade (DE); Uwe Rass, Nürnberg (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 0 days.

(21) Appl. No.: 10/893,650

(22) Filed: Jul. 16, 2004

(65) Prior Publication Data

US 2005/0013456 A1 Jan. 20, 2005

(30) Foreign Application Priority Data

Jul. 16, 2003 (DE) .......................................... 103 32 119

(51) Int. Cl.⁷ .............................................. H04R 25/00
(52) U.S. Cl. ..................... 381/312; 381/318; 381/328; 381/71.6; 381/94.1
(58) Field of Search ................................. 381/312, 317, 381/318, 320, 321, 322, 328, 71.6, 94.1, 380, 324

(56) References Cited

U.S. PATENT DOCUMENTS 5,033,090 A * 7/1991 Weinrich .................... 381/318

FOREIGN PATENT DOCUMENTS

DE 40 10 372 A1 10/1991

* cited by examiner

Primary Examiner—Huyen D. Le
(74) Attorney, Agent, or Firm—Schiff Hardin LLP

(57) ABSTRACT

In the case of a hearing aid device which can be worn in the ear or a hearing aid device with a otoplastic which can be worn in the ear, the penetration of direct sound through a ventilation channel of the hearing aid device or of the otoplastic is prevented. An acoustic signal is picked up from the ventilation channel via a second microphone in a first region of the ventilation channel and phase-shifting it in a filter device in such a way that the direct sound is at least largely eliminated after the phase-shifted signal is emitted into the ventilation channel via a second earphone. The invention offers the advantage that an enlargement of the cross section of the ventilation channel is made possible as a result, even to provide an open supply, without disturbing direct sound getting into the auditory canal of the person wearing the hearing device.

12 Claims, 1 Drawing Sheet

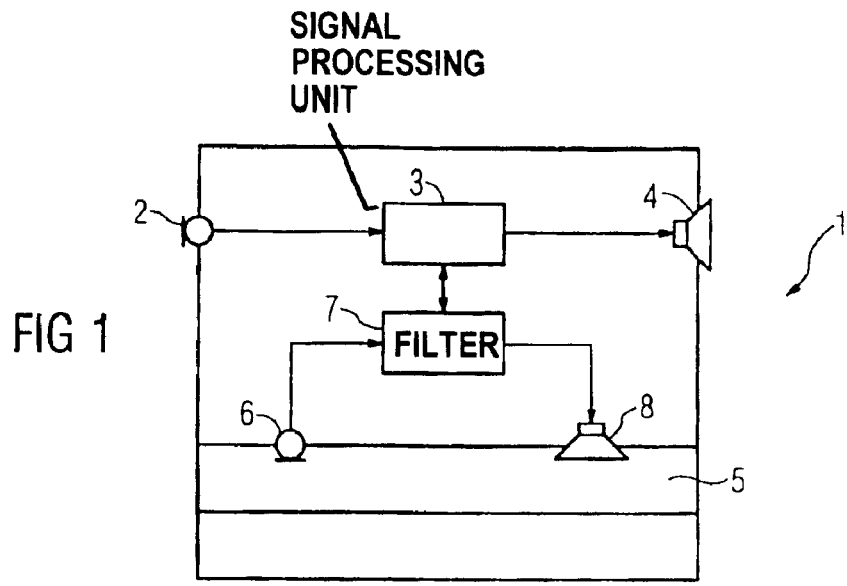
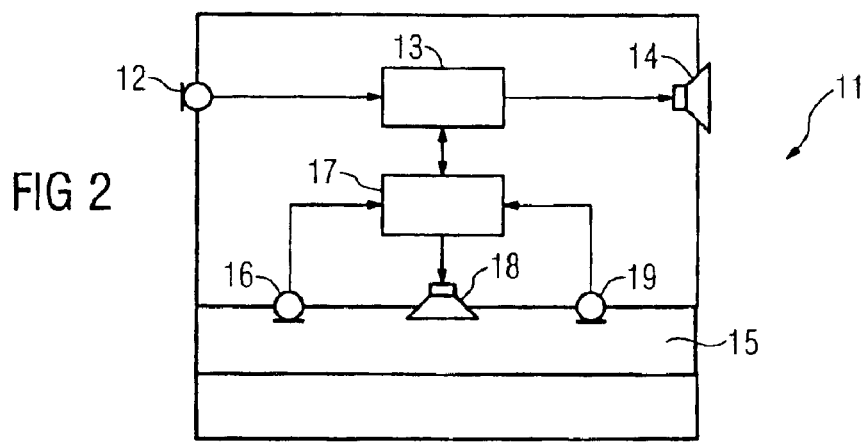
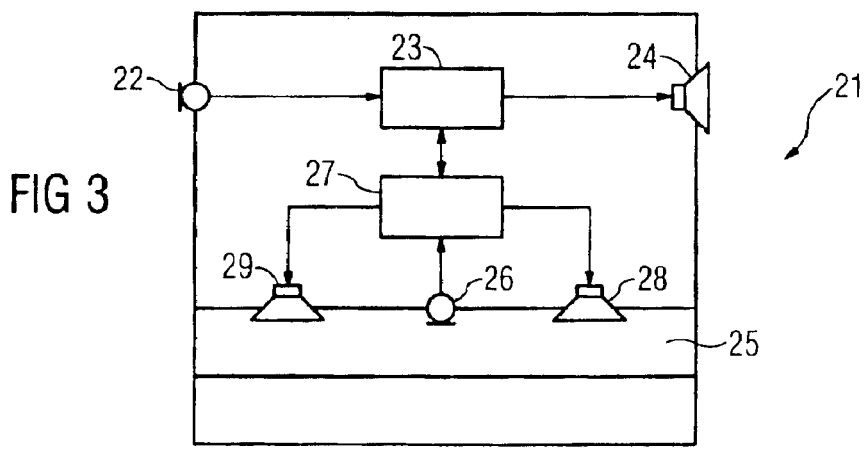

US 6,920,227 B2

ACTIVE NOISE SUPPRESSION FOR A HEARING AID DEVICE WHICH CAN BE WORN IN THE EAR OR A HEARING AID DEVICE WITH OTOPLASTIC WHICH CAN BE WORN IN THE EAR

BACKGROUND OF THE INVENTION

The invention relates to a hearing aid device which can be worn in the ear or a hearing aid device with a otoplastic which can be worn in the ear, which comprises at least a first microphone for picking up a first acoustic signal and emitting a first electrical microphone signal, a signal processing unit, a first earphone for emitting a first earphone signal and a ventilation channel, which is used for ventilating the volume of the auditory canal that is enclosed by the hearing aid device when it is being worn or by the otoplastic when it is being worn.

In the case of a hearing aid device which can be worn in the ear or a hearing aid device with a otoplastic which can be worn in the ear, the housing of the hearing aid device or the otoplastic closes the external auditory canal of an ear with a largely soundproof effect. The housing of the hearing aid device which can be worn in the ear or the otoplastic which can be worn in the ear usually has a ventilation channel passing through it, which serves for ventilating and venting the closed portion of the external auditory canal.

The cross-sectional surface area of this ventilation channel must generally be kept relatively small in order largely to avoid acoustic interference signals which pass through the ventilation channel, thereby bypassing the electrical signal processing by the hearing aid device. However, a large diameter has the advantage of better ventilation and a smaller occlusion effect. Nevertheless, a significant low-frequency direct sound component passes through a ventilation channel with a large cross section into the volume of the auditory canal enclosed by the hearing aid device or the otoplastic. The larger the cross section of the ventilation channel, the higher the limiting frequency below which a notable direct sound enters the auditory canal.

The ventilation channel represents an acoustic bypass with respect to the electrical signal path through the hearing aid device. Interference signals, which usually have a large low-frequency component, can therefore no longer be damped by the electrical signal processing in the hearing aid device. To avoid this effect, the cross section of the ventilation channel must be made as small as possible. As a result, however, adequate ventilation and venting of the enclosed volume of the auditory canal often cannot be ensured any longer.

German patent document DE 40 10 372 A1 discloses a hearing device with an earpiece that can be inserted into the external auditory canal of an ear and has a ventilation channel, in which device an acoustic input signal is picked up by a first microphone and converted into an electrical microphone signal, subjected to signal processing in a signal processing unit and converted back into an acoustic signal and emitted into the auditory canal of the person wearing the hearing device by a first earphone. In the case of the known hearing device, in the ventilation channel there is a second microphone and a second earphone, sound waves generated by the first earphone being picked up by the second microphone, phase-shifted and emitted again by the second earphone, so that sound waves of the first earphone penetrating through the ventilation channel from the enclosed volume of the auditory canal to the outside are largely suppressed.

SUMMARY OF THE INVENTION

The object of the present invention is to avoid direct sound reaching the hearing of a person wearing a hearing device while bypassing the electrical signal processing by the hearing aid device.

This object is achieved in the case of a hearing aid device which can be worn in the ear or a hearing aid device with a otoplastic which can be worn in the ear, which comprises at least a first microphone for picking up a first acoustic signal and emitting a first electrical microphone signal, a signal processing unit, a first earphone for emitting a first earphone signal and a ventilation channel, which is used for ventilating the volume of the auditory canal that is enclosed by the hearing aid device when it is being worn or by the otoplastic when it is being worn, by providing that a second microphone picks up a second acoustic signal from a first region of the ventilation channel and converts it into a second electrical microphone signal, the second electrical microphone signal being fed to a filter device, the filter device emitting an electrical signal to a second earphone and the second earphone emitting into a second region of the ventilation channel, which lies closer to the enclosed volume of the auditory canal than the first region, a second acoustic earphone signal, which at least largely suppresses an acoustic signal penetrating through the ventilation channel from the outside into the enclosed volume of the auditory canal.

The invention offers the advantage that, even in the case of a relatively large cross section of the ventilation channel, direct sound entering the auditory canal from the outside through the ventilation channel is largely avoided.

In the case of a hearing aid device according to embodiments of the invention, an acoustic signal which, in the region of the signal emission into the ventilation channel by the second earphone, is in phase opposition to the acoustic signal penetrating into the ventilation channel from the outside is generated in the ventilation channel while taking into account the distance between the second microphone and the second earphone and also the velocity of sound in air, and consequently at least largely eliminates this outside acoustic signal.

Since the direct sound penetrating through the ventilation channel presents a problem particularly at low frequencies, one embodiment of the invention envisages eliminating the direct sound penetrating through the ventilation channel only in the range of low frequencies. This may take place for example by only a low-frequency acoustic earphone signal being emitted by the second earphone.

The transit time delay, phase shift, and possibly damping of the acoustic signal picked up by the second microphone take place in a filter device of the hearing aid device. This may be implemented by a digital circuit. Alternatively, the phase shift may also take place via a circuit produced by analog technology. In particular, in the case of analog circuit engineering, the necessarily short transmission delays from the second microphone to the second earphone can be implemented particularly easily. Additional A/D or D/A converters are not longer needed.

An embodiment of the invention provides a third microphone that picks up a third acoustic signal from a third region of the ventilation channel that lies closer to the enclosed volume of the auditory canal than the second region, and converts it into a third electrical microphone signal, the third electrical microphone signal also being fed to the filter device. In the filter device there is generated an electrical signal for activating the second earphone, which converts this signal into an acoustic signal and emits it into the ventilation channel, so that an acoustic signal penetrating from the enclosed volume of the auditory canal to the outside is at least largely suppressed. This development offers the advantage that, apart from the acoustic bypass through the ventilation channel, it also suppresses feedback effects which are caused by an acoustic signal being emitted by the first earphone into the auditory canal and returning through the ventilation channel to the first microphone and being picked up by the latter as an acoustic input signal.

An alternative embodiment with respect to the development last mentioned provides, instead of a further microphone, a third earphone, which emits a third acoustic earphone signal into a third region of the ventilation channel that lies further away from the enclosed volume of the auditory canal than the second region, in which the sound pickup by the second microphone takes place, which third earphone signal likewise at least largely suppresses an acoustic signal penetrating from the enclosed volume of the auditory canal to the outside.

The two last-mentioned possibilities for developments share the common feature that an acoustic signal through the ventilation channel that is to be suppressed is initially picked up by a microphone in the direction of propagation of this signal and is phase-shifted in a filter device before an earphone arranged downstream of the microphone in the direction of propagation of the acoustic signal emits the signal filtered in this way into the ventilation channel.

One embodiment of the invention provides that the second microphone and the second earphone are arranged at least partly in the ventilation channel. In this case, it is also possible for the cross section of the ventilation channel to be enlarged in the region of the microphone or the earphone. Furthermore, the second microphone or the second earphone may be arranged directly on the wall of the ventilation channel so that only their acoustic input aperture or acoustic output aperture protrudes into the ventilation channel.

A further alternative provides sound channels between the microphone or the earphone and the ventilation channel. Although this embodiment facilitates the arrangement of the microphone or the earphone in the hearing aid device or in the otoplastic, the transit times of the acoustic signals through these sound channels during the filtering must also be taken into account.

Altogether, the direct sound component in the auditory canal can be considerably reduced by the invention while maintaining the same cross section of the ventilation channel, or a larger cross section of the ventilation channel is possible without causing any loss in the effect of a noise suppression at low frequencies brought about by the electrical signal processing by the hearing aid device.

DESCRIPTION OF THE DRAWINGS

The invention is explained in more detail below on the basis of exemplary embodiments shown in the figures.

FIG. 1 is a block diagram showing a hearing aid device that can be worn in the ear, with a ventilation channel in which a second microphone and a second earphone are arranged;

FIG. 2 is a block diagram showing a hearing aid device which can be worn in the ear, with two microphones and an earphone in the ventilation channel; and FIG. 3 is a block diagram showing a hearing aid device with a microphone and two earphones in the ventilation channel.

DETAILED DESCRIPTION OF THE PREFERRED EMBODIMENTS

The following describes various exemplary embodiments of the invention. FIG. 1 shows a simplified block diagram of a hearing aid device 1 with a microphone 2 for picking up an acoustic input signal and converting it into an electrical microphone signal. The electrical microphone signal is fed to a signal processing unit 3 in which the signal processing and frequency-dependent amplification to compensate for the individual hearing loss of a person wearing the hearing device take place. The processed electrical signal is finally fed to an earphone 4, which converts the electrical signal into an acoustic signal and emits it into an auditory canal of the person wearing the hearing device.

A ventilation channel 5 is provided for ventilating the volume of the auditory canal enclosed by the hearing aid device 1. The hearing aid device 1 also has a second microphone 6, which picks up an acoustic signal in a first region of the ventilation channel 5, converts it into an electrical signal, and feeds it to a filter device 7. From the filter device 7 there emerges an electrical signal which is converted into an acoustic signal and emitted into the ventilation channel 5 by way of a second earphone 8.

The second microphone 6 and the second earphone 8 are arranged next to each other in the ventilation channel 5 in such a way that the second microphone 6 is closer to the side of the ventilation channel 5 that is facing away from the head of the person wearing the hearing device when the hearing aid device 1 is being worn and the second earphone 8 lies closer to the opposite end of the ventilation channel 5, which is facing toward the head of the person wearing the hearing device.

Direct sound penetrating through the ventilation channel from the outside into the auditory canal is therefore initially picked up by the second microphone 6 and, taking into account the transit time of the acoustic signal between the second microphone 6 and the second earphone 8, phase-shifted by the filter device 7 in such a way that an elimination of the direct sound in the ventilation channel 5 takes place by emitting this phase-shifted signal using the second earphone 8.

This provides the advantage of overcoming the acoustic bypass that is represented by the ventilation channel 5 with respect to the electrical signal path through the hearing aid device 1, extending from the microphone 2 via the signal processing unit 3 and the earphone 4. This makes it possible for the cross section of the ventilation channel 5 to be enlarged up to a point where it provides an open supply.

In the case of a preferred embodiment of the invention, there is an electrical connection for the signal transmission between the signal processing unit 3 and the filter device 7, so that the active noise suppression according to the invention is only active, for example, whenever a specific hearing program is set on the signal processing unit 3. Furthermore, the active noise suppression may also take place according to the invention in dependence on the ambient acoustic situation at a given instant, for example, in such a way that this is only carried out if the acoustic input signal picked up by the microphone 2 exceeds a specific signal level.

An embodiment of the invention is represented in FIG. 2. It is also the case here that in a hearing aid device 11 picks up of an acoustic input signal with a first microphone 12 and processes the signal by a signal processing unit 13 and finally emits an acoustic output signal into the auditory canal of a person wearing the hearing device via a first earphone 14.

The hearing aid device 11 also has a ventilation channel 15 from which an acoustic signal is picked up via a second microphone 16, converted into an electrical signal, and fed to a filter device 17. The signal phase-shifted in the filter device 17 is emitted via a second earphone 18 into the ventilation channel 15, it also being the case here that the second earphone 18 is arranged closer to the end of the ventilation channel 15 that is facing toward the head than the second microphone 16.

As a difference in comparison with the previous exemplary embodiment, the hearing aid device 11 also comprises a third microphone 19, which picks up a third acoustic signal and converts it into a third electrical microphone signal, which is fed to the filter device 17 in a way similar to the second electrical microphone signal of the second microphone 16. A phase shift is also carried out by the filter device 17 for the microphone-earphone pair 19,18, so that an acoustic signal coming from the first earphone 14 and passing through the ventilation channel 15 to the outside is eliminated in the region of the second earphone 18.

This further development offers the advantage that complete elimination of all the acoustic signals passing through the ventilation channel 15 can take place. In addition to the advantages already mentioned, feedback effects are consequently also largely avoided in the case of the hearing aid device 11.

FIG. 3 shows an alternative embodiment with respect to the exemplary embodiment according to FIG. 2. It is also the case with this exemplary embodiment that in a hearing aid device 21 an acoustic input signal is picked up by a microphone 22, converted into an electrical microphone signal and fed to a signal processing unit 23. The processed signal is converted by an earphone 24 into an acoustic signal and emitted into the auditory canal of the person wearing the hearing device.

It is also the case with the exemplary embodiment according to FIG. 3 that an acoustic signal getting into the auditory canal from the outside through a ventilation channel 25 initially passes a second microphone 26 and subsequently a second earphone 28. In a filter device 27, the acoustic signal picked up by the second microphone 26 and converted into an electrical microphone signal is phase-delayed, so that in the region of the sound emission by the second earphone 28 the sound signal penetrating into the auditory canal from the outside is substantially eliminated.

Furthermore, an acoustic signal is also picked up by the second microphone 26, emitted by the first earphone 24 into the enclosed volume of the auditory canal, and conducted to the outside through the ventilation channel 25. A phase shift is also performed by the filter device 27 on the resultant second microphone signal so that in the region of a third earphone 29 the acoustic signal conducted to the outside through the ventilation channel 25 is eliminated. This embodiment also offers the advantage that both an acoustic signal passing from the outside inward and an acoustic signal passing from the inside outward through the ventilation channel 25 can be suppressed with a very short reaction time.

In summary, in the case of a hearing aid device which can be worn in the ear or a hearing aid device with otoplastic which can be worn in the ear, the penetration of direct sound through a ventilation channel 5, 15, 25 of the hearing aid device or of the otoplastic is prevented. For this purpose, the above embodiments invention provide for picking up an acoustic signal from the ventilation channel 5, 15, 25 via a second microphone 6, 16, 26 in a first region of the ventilation channel 5, 15, 25 and phase-shifting it in a filter device 7, 17, 27 in such a way that the direct sound is at least largely eliminated after the phase-shifted signal is emitted into the ventilation channel 5, 15, 25 via a second earphone 8, 18, 28.

The embodiments of the invention offers the advantage that an enlargement of the cross section of the ventilation channel 5, 15, 25 is made possible as a result, even to provide an open supply, without disturbing direct sound getting into the auditory canal of the person wearing the hearing device.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

What is claimed is:

1. A hearing aid device that can be worn in the ear or a hearing aid device with otoplastic that can be worn in the ear, comprising:

a first microphone for picking up a first acoustic signal and emitting a first electrical microphone signal;

a first earphone for emitting a first earphone signal;

a signal processing unit connected to the first microphone and the first earphone;

a filter connected to the signal processing unit;

a ventilation channel configured for ventilating a volume of an auditory canal that is enclosed by the hearing aid device when it is being worn or by the otoplastic when it is being worn, the ventilation channel having a first region and a second region, the second region being located closer to the enclosed volume of the auditory canal than the first region;

a second earphone configured to emit a second acoustic earphone signal into the second region; and a second microphone configured for picking up a second acoustic signal from the first region of the ventilation channel and converting it into a second electrical microphone signal, the second electrical microphone signal being fed to the filter, the filter emitting an electrical signal to the second earphone, and the second acoustic earphone signal at least largely suppressing an acoustic signal penetrating through the ventilation channel from outside into the enclosed volume of the auditory canal.

2. The device as claimed in claim 1, further comprising:

a third microphone configured to pick up a third acoustic signal from a third region of the ventilation channel that lies closer to the enclosed volume of the auditory canal than the second region and converts it into a third electrical microphone signal, the third electrical microphone signal being fed to the filter device and the filter device configured to emit an electrical signal to the second earphone, which at least largely suppresses an acoustic signal penetrating from the enclosed volume of the auditory canal to the outside.

3. The device as claimed in claim 2, further comprising:

a sound channel via which the third microphone is connected to the ventilation channel.

4. The device as claimed in claim 1, further comprising:

a third earphone configured to emit a third acoustic earphone signal into a fourth region of the ventilation channel that lies further away from the enclosed volume of the auditory canal than the second region, the third earphone signal at least largely suppressing an acoustic signal penetrating from the enclosed volume of the auditory canal to the outside.

5. The device as claimed in claim 3, further comprising:

a sound channel via which the third earphone is connected to the ventilation channel.

6. The device as claimed in claim 1, wherein the second microphone is arranged at least partly in the ventilation channel.

7. The device as claimed in claim 1, wherein the second earphone is arranged at least partly in the ventilation channel.

8. The device as claimed in claim 1, wherein the third microphone is arranged at least partly in the ventilation channel.

9. The device as claimed in claim 1, wherein the third earphone is arranged at least partly in the ventilation channel.

10. The device as claimed in claim 1, wherein the second microphone is connected to the ventilation channel via a sound channel.

11. The device as claimed in claim 1, further comprising:

a sound channel via which the second earphone is connected to the ventilation channel.

12. The device as claimed in claim 1, further comprising:

one or more hearing programs configured for adapting signal processing in the hearing aid device to different ambient situations that can be set on the hearing aid device, and the suppression of an acoustic signal passing through the ventilation channel taking place depending on the hearing program that is set.

* * * * *